United States Patent [19]

Kajiyama et al.

[11] 3,943,134

[45] Mar. 9, 1976

[54] PROCESS FOR PREPARING ACETONIN

[75] Inventors: Shigeo Kajiyama; Takamitsu Kobayashi; Keiro Yoshizue, all of Kamakura, Japan

[73] Assignee: Sankyo Company Limited, Japan

[22] Filed: Oct. 18, 1974

[21] Appl. No.: 515,815

[30] Foreign Application Priority Data
Nov. 8, 1973 Japan............................ 48-125753
May 22, 1974 Japan............................ 49-57541

[52] U.S. Cl............................................. 260/251 R
[51] Int. Cl.²........................................ C07D 239/04
[58] Field of Search............................. 260/251 R

[56] References Cited
OTHER PUBLICATIONS
Industrial J. Chem. 6, pp. 143–151, (1953).
Helv. Chim. Acta., 30, pp. 1114–1119, (1947).

Bradbury et al., [J.C.S.], (1947), pp. 1394–1399.

*Primary Examiner*—Lewis Gotts
*Assistant Examiner*—D. R. Phillips
*Attorney, Agent, or Firm*—Toren, McGeady and Stanger

[57] ABSTRACT

2,2,4,4,6-Pentamethyl-2,3,4,5-tetrahydropyrimidine, called acetonin, is prepared by reacting acetone with ammonia in the presence of an ammonium halide catalyst and in the presence of from 0.01 to 0.5 mole % (based on acetone) of a promoter selected from the group consisting of: bromine; iodine; iodine trichloride; alkali metal iodides; lithium rhodanide, bromide, nitrate and cyanide; ammonium iodide, rhodanide, bromide, nitrate and sulfide; ammonium salts of carboxylic acids and of sulfonic acids; salts of nitrogen-containing organic bases with carboxylic acids and with sulfonic acids; aliphatic amine hydroiodides; carboxylic acids; and sulfonic acids.

8 Claims, No Drawings

PROCESS FOR PREPARING ACETONIN

BACKGROUND OF THE INVENTION

The present invention relates to a process for preparing 2,2,4,4,6-pentamethyl-2,3,4,5-tetrahydropyrimidine, which is commonly known by the trivial name "acetonin" and which has the formula:

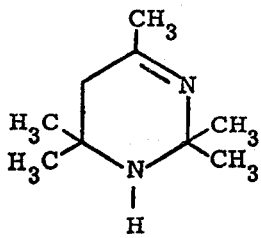

Acetonin is used to prepare triacetonamine from which, in turn, may be produced a wide variety of triacetonamine derivatives, which are useful as stabilizers for synthetic high molecular weight polymers. As world-wide use of synthetic polymers increases, the demand for triacetonamine derivatives as polymer stabilizers increases correspondingly and there is, accordingly, a demand for a process for preparing acetonin economically on a commercial scale.

Bradbury et al [J.C.S. (1947), 1394] disclose a process for preparing acetonin by reacting acetone with ammonia in the presence of a catalyst; various ammonium salts and halides of aliphatic amines were used as catalyst, although it would appear that best results were achieved using ammonium chloride. It was also found that the yield of product could be increased by using calcium chloride as a promoter. Matter[Helv. Chim. Acta., 30, 1114, (1947)] discloses the production of acetonin by reacting acetone and ammonia in the presence of an ammonium chloride catalyst and calcium chloride as a promoter in an amount of 27 mole %. Matter also discloses that calcium bromide, calcium iodide, lithium chloride or lithium bromide may be used in place of calcium chloride in this reaction.

In these known processes, where the catalyst is an ammonium halide or the like alone, the reaction proceeds so slowly that 10 or more hours are required in order to obtain the maximum yield. Moreover, if the reaction is carried out in the presence of a calcium salt as promoter, a viscous mass containing the calcium salt forms during the course of the reaction and this mass sticks to the wall of the reaction vessel, which reduces thermal efficiency and necessitates the use of a powerful stirring device. This, therefore, complicates the reaction procedure. Furthermore, since this mass is insoluble in the reaction mixture, treatment of the product to obtain acetonin free from the calcium salt is difficult and complicated. Accordingly, an improved, commercially attractive, process for the preparation of acetonin is desired by the art.

BRIEF SUMMARY OF INVENTION

It is, therefore, an object of the present invention to provide a process for preparing acetonin from acetone and ammonia in high yield and with a short reaction time, so as to provide a process which may be carried out economically on an industrial scale.

This object is achieved by reacting ammonia and acetone in the presence of an ammonium halide catalyst and in the additional presence of from 0.01 to 0.5 mole %, based on acetone starting material, of a promoter different from said ammonium halide catalyst and selected from the group consisting of: bromine; iodine; iodine trichloride; alkali metal iodides; lithium rhodanide (i.e. thiocyanate), bromide, nitrate and cyanide; ammonium iodide, rhodanide, bromide, nitrate and sulfide; ammonium salts of carboxylic acids and of sulfonic acids; salts of nitrogen-containing organic bases with carboxylic acids and with sulfonic acids; hydroiodides of aliphatic amines containing from 1 to 12 carbon atoms; carboxylic acids; and sulfonic acids.

DETAILED DESCRIPTION OF INVENTION

The amount of promoter employed in the process of the present invention is far less than the amount of calcium chloride or the like employed in the prior art; thus, whereas the amount of calcium chloride or the like employed in the prior art varies from 7 mole % (Bradbury et al) to 27 mole % (Matter), based on acetone, the promoter employed in the process of the present invention is used in an amount of from 0.01 to 0.5 mole %, preferably from 0.1 to 0.4 mole %, based on acetone. The most preferred amount is 0.1 mole %. It could not have been anticipated that such a small amount of promoter in addition to the ammonium halide could bring about the excellent results achieved in the process of the present invention; thus, the process of the invention can produce acetonin in a yield of about 85% or even more of theory in a reaction time of from 3 to 6 hours. By way of contrast, if ammonium chloride is employed alone as catalyst, without promoter, a yield of only about 55% is achieved in the same reaction time, this increasing to about 70%, under the same conditions, if 7 mole % of calcium chloride is used together with the ammonium chloride catalyst.

The promoter employed in the present invention is selected from the group consisting of: bromine; iodine; iodine trichloride; alkali metal iodides; lithium rhodanide, bromide, nitrate and cyanide; ammonium iodide, rhodanide, bromide, nitrate and sulfide; ammonium salts of carboxylic acids and of sulfonic acids; salts of nitrogencontaining organic bases with carboxylic acids and with sulfonic acids; hydroiodides of aliphatic amines having from 1 to 12 carbon atoms; carboxylic acids; and sulfonic acids.

Examples of alkali metal iodides which may be used as promoters include sodium iodide, potassium iodide and lithium iodide.

Examples of carboxylic acids which themselves may be used as promoters or whose ammonium salts or salts with nitrogen-containing organic bases may be used as promoters include aliphatic and aromatic, monocarboxylic, dicarboxylic and tricarboxylic acids, for example: saturated aliphatic monocarboxylic acids, such as formic acid, acetic acid, propionic acid, butyric acid, lauric acid, palmitic acid, and stearic acid; unsaturated aliphatic monocarboxylic acids, such as acrylic acid and methacrylic acid; halocarboxylic acids, such as chloroacetic acid, dichloroacetic acid, trichloroacetic acid and trifluoroacetic acid; saturated aliphatic dicarboxylic acids, such as malonic acid, succinic acid, adipic acid, suberic acid, tartaric acid and malic acid; unsaturated aliphatic dicarboxylic acids, such as fumaric acid and maleic acid; saturated aliphatic tricarboxylic acids, such as citric acid; aromatic monocarboxylic acids, such as benzoic acid, the toluic acids and the naphthoic acids; aromatic dicarboxylic acids, such as phthalic acid and terephthalic acid; and aromatic tricarboxylic acids, such as trimellitic acid.

Examples of sulfonic acids which may themselves be used as promoters or whose ammonium salts or whose salts with nitrogen-containing organic bases may be used as promoters include: aliphatic sulfonic acids, such as methanesulfonic acid; and aromatic sulfonic acids, such as benzenesulfonic acid, p-toluenesulfonic acid, naphthalene-sulfonic acid and naphthalene-1,5-disulfonic acid.

We particularly perfer carboxylic acids and sulfonic acids whose pKa values are below 5.

Ammonium salts or salts of nitrogen-containing organic bases with the above-exemplified carboxylic and sulfonic acids may also be used as promoters in the process of the invention. The nitrogen-containing organic base used to form such a salt may be an aliphatic, alicyclic or aromatic, primary, secondary or tertiary amine, a saturated or unsaturated nitrogen-containing heterocyclic base, urea or thiourea. Specific examples of such bases include: aliphatic primary amines, such as methylamine, ethylamine, n-butylamine, octylamine, dodecylamine and hexamethylenediamine; aliphatic secondary amines, such as dimethylamine, diethylamine, di-n-propylamine, diisobutylamine, di-n-pentylamine, and di-n-hexylamine; aliphatic tertiary amines, such as trimethylamine, triethylamine, tri-n-propylamine and tri-n-butylamine; alicyclic primary amines, such as cyclohexylamine; aromatic primary amines, such as aniline, the toluidines, benzylamine, the naphthylamines and benzidine; aromatic secondary amines, such as N-methylaniline, N-ethylaniline, dibenzylamine and diphenylamine; aromatic-tertiary amines, such as N,N-dimethylaniline, N,N-diethylaniline, tribenzylamine and triphenylamine; saturated and unsaturated nitrogen-containing heterocyclic bases, such as pyrrolidine, piperidine, N-methyl-2-pyrrolidone, pyrazolidine, piperazine, pyridine, picoline, indoline, quinuclidine, morpholine, N-methylmorpholine, 1,4-diazabicyclo[2,2,2]-octane, acetonin or triacetonamine; urea; and thiourea.

Examples of the lithium and ammonium salts which may be used in the process of the invention are: lithium rhodanide (LiSCN); ammonium rhodanide (NH$_4$SCN); lithium bromide (LiBr); ammonium bromide (NH$_4$Br); lithium nitrate (LiNO$_3$); and ammonium nitrate (NH$_4$NO$_3$).

The preferred promoters used in the process of the invention are: bromine; iodine; iodine trichloride; ammonium iodide; alkali metal iodides; hydroiodides of aliphatic amines having from 2 to 8 carbon atoms; ammonium sulfide, rhodanide, bromide or nitrate; lithium cyanide, rhodanide, bromide or nitrate; haloacetic acids; methanesulfonic acid; benzenesulfonic acid; p-toluenesulfonic acid; ammonium formate; an ammonium haloacetate; ammonium methane-sulfonate; ammonium benzenesulfonate; and ammonium p-toluene-sulfonate.

Best results have been achieved with the following promoters: iodine; iodine trichloride; ammonium iodide; sodium iodide; potassium iodide; lithium iodide; triethylamine hydroiodide; lithium rhodanide; ammonium rhodanide; lithium bromide; ammonium bromide; and ammonium sulfide.

The main catalyst used in the process of the invention is an ammonium halide, such as ammonium chloride, ammonium bromide or ammonium iodide; for best results, this is employed in an amount greater than 0.2 mole % based on acetone and is preferably employed in an amount of from 1 to 50 mole %, based on acetone. The reaction preferably takes place in the presence of a solvent, such as methanol or ethanol and may be effected by introducing the required amount of gaseous ammonia into a mixture of acetone, solvent (if desired), catalyst and promoter and heating this mixture at a temperature of from 20° to 35°C, preferably from 25° to 30°C, for the required reaction time, which will generally vary from about 3 to about 6 hours. The amount of ammonia introduced may vary from the theoretical stoichiometric amount to an amount sufficient to saturate the reaction mixture. In contrast to the prior art processes, no mass is formed by the catalyst promoter during the reaction, since the promoter employed in the present invention is either soluble in the reaction mixture or, even if it is insoluble, is employed in such a small amount that any deposits formed are negligible. Accordingly, carrying out the process of the invention in practice is quite simple.

The reaction of acetone with ammonia produces substantial quantities of water in addition to the desired acetonin, according to the following equation:

$$3CH_3 \cdot CO \cdot CH_3 + 2NH_3 \longrightarrow$$

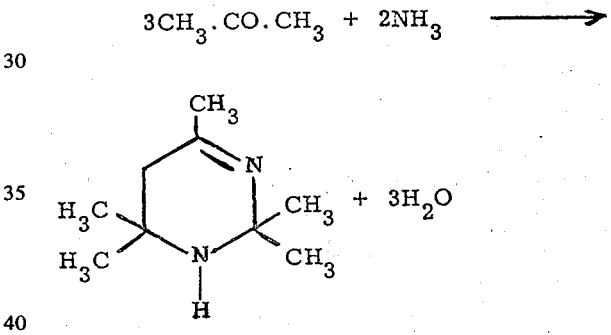

$$+ 3H_2O$$

The desired product, acetonin, is, therefore, obtained as an essentially homogeneous solution; it may easily be recovered from this solution by, for example, addition of an aqueous alkaline solution, e.g. aqueous sodium hydroxide, which causes the solution to separate into two phases, an aqueous phase containing the added alkali and an oily (upper) phase containing the acetonin, generally in the form of the hydrate. If, for example, a 40% aqueous sodium hydroxide solution is employed, the oily upper phase is acetonin monohydrate (plus unused reactants and any impurities); if, on the other hand, solid sodium hydroxide is employed in place of the aqueous alkaline solution, the upper phase will normally consist of a lower hydrate of acetonin, e.g. acetonin. 0.5 H$_2$O.

Since the subsequent reaction of acetonin to produce triacetonamine requires 1 mole of water per mole of acetonin, it is generally convenient to recover the acetonin in the form of its monohydrate. However, if desired, it may be recovered in an essentially anhydrous form or, as described above, as a lower hydrate, or, if recovered as a hydrate, it may subsequently be dehydrated. Dehydration may be effected, for example, over sodium hydroxide or sulfuric acid or by distillation alone or with benzene as entrainer; since sulfuric acid tends to decompose the acetonin, a distillation method is preferred.

The acetonin prepared by the process of the present invention, preferably in the form of the monohydrate, may be used to prepare triacetonamine, e.g. by the following process: acetone is added to the acetonin in an amount equal to or up to about three times as much as the amount of acetone used to prepare the acetonin; where the acetonin is anhydrous or is in the form of a lower hydrate, water is added to an amount equimolar with the acetonin; and the mixture is heated at a temperature of from 20° to 65°C, preferably at reflux temperature, thereby yielding triacetonamine.

The invention is further illustrated by the following non-limiting Examples.

EXAMPLE 1

17.2 g of ammonium chloride and 0.4 g of iodine were mixed with 160.5 g of acetone. 45 g of gaseous ammonia were then passed into this mixture over a period of 6 hours, whilst maintaining the temperature of the mixture at 25°–30°C. At the end of this time, 66 ml of a 48% aqueous sodium hydroxide solution were added to the reaction mixture, which separated into two phases. The aqueous phase was removed using a separating funnel, giving 155.2 g of crude acetonin having an acetonin content of 77.9%; this represented a yield of 85.1% of theory based on the acetone starting material.

EXAMPLE 2

13.2 g of ammonium chloride and 0.3 g of sodium iodide were mixed with 120 g of acetone. 35.2 g of gaseous ammonia were then passed into the mixture over a period of 4 hours, maintaining the reaction temperature at 25°–30°C. When the reaction was complete, the reaction mixture was treated in the manner described in Example 1, giving 109.3 g of crude acetonin having an acetonin content of 84.5%. This represented an acetonin yield of 87% of theory, based on the acetone starting material.

By way of contrast, when this reaction was repeated with no sodium iodide present, an acetonin yield of 55% was achieved after 4 hours. A reaction period of 12 hours was required in order to obtain a yield of 85% of theory.

EXAMPLE 3

The procedure described in Example 2 was repeated, except that the sodium iodide was replaced by 0.34 g of potassium iodide. There were obtained 105.7 g of crude acetonin having an acetonin content of 85.5%. This represented a yield of 85% of theory, based on acetone starting material.

EXAMPLES 4 to 18

1.1 g of ammonium chloride and 0.4 mole % (based on acetone) of each in turn of the promoters set out in the following Table were mixed with 30 g of acetone. 8.8 g of gaseous ammonia were passed into the mixture and absorbed thereby over a period of 4 hours, during which time the temperature of the mixture was maintained at 25°–30°C. When the reaction was complete, 15 ml of a 48% aqueous sodium hydroxide solution were added to the reaction mixture, thereby separating the mixture into two phases. The aqueous phase was removed by means of a separating funnel, leaving an oily phase comprising impure acetonin monohydrate.

The acetonin content of this oily phase was then determined. The yields of acetonin, based on acetone starting material, are also shown in the Table.

As a control, the experiment was repeated, except that no promoter was used. The results of this control experiment are also shown in the Table.

Table

| Example No. | Promoter | Yield of acetonin (%) |
|---|---|---|
| 4 | bromine ($Br_2$) | 72.9 |
| 5 | iodine trichloride ($ICl_3$) | 86.1 |
| 6 | ammonium iodide ($NH_4I$) | 80.5 |
| 7 | triethylamine hydroiodide | 81.1 |
| 8 | lithium rhodanide (LiSCN) | 85.4 |
| 9 | ammonium rhodanide ($NH_4SCN$) | 98.9 |
| 10 | lithium bromide (LiBr) | 84.3 |
| 11 | ammonium bromide ($NH_4Br$) | 81.6 |
| 12 | lithium nitrate ($LiNO_3$) | 77.1 |
| 13 | ammonium nitrate ($NH_4NO_3$) | 76.7 |
| 14 | lithium cyanide (LiCN) | 71.9 |
| 15 | ammonium sulfide [$(NH_4)_2S$] | 82.7 |
| 16 | chloroacetic acid | 79.9 |
| 17 | p-toluenesulfonic acid | 76.8 |
| 18 | ammonium formate | 72.1 |
| Control | none | 60.0 |

We claim:

1. A process for the preparation of acetonin by reacting acetone with ammonia in the presence of an ammonium halide catalyst and in the additional presence of from 0.01 to 0.5 mole & based on the acetone of a promoter different from said catalyst and selected from the group consisting of bromine, iodine, iodine trichloride, ammonium iodide, alkali metal iodides, hydroiodides of aliphatic amines having from 1 to 12 carbon atoms, ammonium sulfide, ammonium rhodanide, ammonium bromide, ammonium nitrate, lithium cyanide, lithium rhodanide, lithium bromide, lithium nitrate, haloacetic acids, methanesulfonic acid, benzenesulfonic acid, p-toluenesulfonic acid, ammonium formate, ammonium halocacetates, ammonium methanesulfonate, ammonium benzenesulfonate and ammonium p-toluenesulfonate.

2. A process as claimed in claim 1, wherein said promoter is selected from the group consisting of iodine, iodine trichloride, ammonium iodide, sodium iodide, potassium iodide, lithium iodide, triethylamine hydroiodide, lithium rhodanide, ammonium rhodanide, lithium bromide, ammonium bromide and ammonium sulfide.

3. A process as claimed in claim 1, wherein said promoter is selected from the group consisting of iodine, sodium iodide and potassium iodide.

4. A process as claimed in claim 1, wherein said promoter is employed in an amount of from 0.1 to 0.4 mole %.

5. A process as claimed in claim 1, wherein said catalyst is ammonium chloride, ammonium bromide or ammonium iodide.

6. A process as claimed in claim 5, wherein said catalyst is employed in an amount of from 1 to 50 mole %.

7. A process as claimed in claim 1, effected at a temperature of from 20° to 35°C.

8. A process as claimed in claim 1, wherein said acetonin is recovered from the reaction mixture in the form of acetonin monohydrate.

* * * * *